US007654674B2

(12) United States Patent  
Hegels et al.

(10) Patent No.: US 7,654,674 B2
(45) Date of Patent: Feb. 2, 2010

(54) METHOD AND APPARATUS FOR DETERMINING THE VISUAL ACUITY OF AN EYE

(75) Inventors: Ernst Hegels, Kirchheim (DE); Gerhard Youssefi, Landshut (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 12/093,500

(22) PCT Filed: Nov. 8, 2006

(86) PCT No.: PCT/EP2006/010706

§ 371 (c)(1),
(2), (4) Date: May 13, 2008

(87) PCT Pub. No.: WO2007/057114

PCT Pub. Date: May 24, 2007

(65) Prior Publication Data

US 2008/0246916 A1 Oct. 9, 2008

(30) Foreign Application Priority Data

Nov. 16, 2005 (DE) .................. 10 2005 054 691

(51) Int. Cl.
*A61B 3/00* (2006.01)
(52) U.S. Cl. .................. 351/246; 351/205; 351/221
(58) Field of Classification Search .............. 351/205, 351/212, 221, 246, 247
See application file for complete search history.

(56) References Cited

U.S. PATENT DOCUMENTS

| 5,360,010 | A | 11/1994 | Applegate |
| 5,777,719 | A | 7/1998 | Williams et al. |
| 6,199,986 | B1 * | 3/2001 | Williams et al. ............ 351/221 |
| 6,499,843 | B1 | 12/2002 | Cox et al. |
| 6,659,613 | B2 | 12/2003 | Applegate et al. |
| 2003/0053026 | A1 | 3/2003 | Roorda |
| 2003/0063815 | A1 | 4/2003 | Watanabe |
| 2004/0119942 | A1 | 6/2004 | Applegate et al. |
| 2004/0130678 | A1 | 7/2004 | Hirohara et al. |

FOREIGN PATENT DOCUMENTS

| EP | 1158338 A2 | 11/2001 |
| WO | WO 95/27453 A1 | 10/1995 |
| WO | WO 01/82791 A1 | 11/2001 |
| WO | WO 02/30273 A1 | 4/2002 |
| WO | WO 03/020121 A1 | 3/2003 |
| WO | WO 03/092485 A1 | 11/2003 |
| WO | WO 2004/112576 A2 | 12/2004 |

OTHER PUBLICATIONS

Roorda, "A Review of Optics presentation," University of Houston, Feb. 2003.

* cited by examiner

*Primary Examiner*—Huy K Mai

(57) ABSTRACT

The invention relates to a method for determining the visual acuity of an eye and a respective apparatus. The method comprises the steps of: providing the wavefront information of the eye, generating a point spread function based on the wavefront information of the eye, said point spread function representing a specific intensity distribution for a corresponding pupil size. After comparing the intensities of the point spread function with a selectable intensity level of intensity, those parts of the point spread function having an intensity being larger than the selectable intensity level are determined as a relevant part of the point spread function.

36 Claims, 10 Drawing Sheets

Fig.1: Typical wavefront of a best corrected eye. The wavefront is shown for the pupil plane of eye.

Fig.2: The normalized PSF (at the retina) originating from the wavefront shown in Figure 1

Fig.3: Parts of the PSF shown in Figure 2 which are above 50% of the maximum of intensity Fig.4: Parts of the PSF shown in Figure 2 which are above 60% of the maximum of intensity Fig.5: Parts of the PSF shown in Figure 2 which are above 65% of the maximum of intensity Fig.6: Parts of the PSF shown in Figure 2 which are above 75% of the maximum of intensity Fig.7: Parts of the PSF shown in Figure 2 which are above 50% of the maximum of intensity. The convex hull is shown by the solid line. The dashed circle circumscribes the relevant parts.

Fig.8: Parts of the PSF shown in Figure 2 which are above 50% of the maximum of intensity. The ellipse is fitted by using the area of convex hull and circle shown in Figure 7 are used for determination of the short and long axis of the ellipse.

METHOD AND APPARATUS FOR DETERMINING THE VISUAL ACUITY OF AN EYE

CROSS REFERENCE

This application claims the benefit of International Application No. PCT/EP2006/010706 filed May 16, 2007.

BACKGROUND OF THE INVENTION

The present invention relates to a method and apparatus for determining the visual acuity of an eye by analysing the wave front information of the eye, in particular by analysing a corresponding point spread function (PSF).

WO 02/30273 A1 relates to the determination of ocular refraction from wavefront aberration data and an optimum customized correction is designed. The eye's wave aberration is measured by using a detector such as a Shack-Hartmann detector. From the aberration, an image metric is calculated, and the second-order aberrations which optimize that metric are determined. From that optimization, the refractive correction required for the eye is determined. The image metric is one of several metrics indicating the quality of the image on the retinal plane or a proxy for such a metric. The required refractive correction can be used to form a lens or to control eye surgery. It further relates to five different metrics of image quality, i.e. Strehl ratio, entropy of the point spread function (PSF), variance of the PSF, MTFa, defined as the integral of the modulation transfer function (MTF) within the range of discriminable frequencies, from 0 to 60 c/deg, and CSFa, defined as the integral of the contrast sensitivity function (CSF), which is obtained as the product of the MTF and the neural CSF. Further reference is made to the encircled energy of the PSF that falls within a small area around the peak of the image. As a metric the encircled energy calculated as the fraction of light in the PSF within an area corresponding to the Airy disk is mentioned. This document is silent on how to provide a value for the visual acuity.

WO 03/092485 A1 relates to a vision metric, called the sharpness metric, which indicates the subjective sharpness of a patient's vision by taking into account both the wavefront aberration and the retinal response to the image. A retinal image quality function such as the point spread function is convolved by a neural quality function, and the maximum of the convolution over the retinal plane provides the sharpness metric. The sharpness metric can be used to control eye surgery or the fabrication of a lens.

U.S. Pat. No. 5,777,719 describes a method and apparatus for improving vision and the resolution of retinal images. It specifically relates to a Hartmann-Shack wavefront sensor for acquiring the wavefront information of an eye. More specifically, a point source produced on the retina of a living eye by a laser beam is reflected from the retina and received at a lenslet array of a Hartmann-Shack wavefront sensor such that each of the lenslets in the lenslet array forms an aerial image of the retinal point source on a CCD camera located adjacent the lenslet array. The output signal from the CCD camera is acquired by a computer which processes the signal and produces a correction signal which may be used to control a compensating optical or wavefront compensation device such as a deformable mirror. It may also be used to fabricate a contact lens or intraocular lens, or to guide a surgical procedure to correct the aberrations of the eye. For showing the result of the correction of aberrations of the eye, reference is made to the point spread function (PSF) computed from the wave aberration. It is shown that after compensation, the PSF or a particular subject has a full-width at half height (FWHH) of 2.0 microns, which shall be close to the value of 1.9 microns expected from diffraction alone.

In US 2004/0119942 A1 and U.S. Pat. No. 6,659,613 B2, methods and systems for measuring local scattering and aberration properties of optical media are described. A Hartmann-Shack calibration image of a measurement system is acquired to define a first plurality of point spread functions. A Hartmann-Shack test image of the medium is acquired to define a second plurality of point spread functions. A shift is determined between the test image and the calibration image. A point spread of each of the second plurality of point spread functions is measured, each of the second plurality of point spread functions including a component due to optical aberration of the medium and a component due to scatter. The component due to optical aberration is determined using the shift. The component due to optical aberration is deconvolved to determine the component due to scatter.

U.S. Pat. No. 6,499,843 B1 relates to a customized vision correction method which comprises obtaining a wavefront aberration measurement of a patient's eye and providing a display of the wave front aberration measurement in the form of either a picture, a computer simulation, a graphic display, and a mathematical representation of the wavefront. Specific reference is made to analyzing a point spread function for determining a Strehl ratio.

The object of the present invention is to provide a method and an apparatus for determining the visual acuity of an eye by analysing the wavefront information of the eye.

This object is solved with the features of the claims.

The present invention specifically allows to determine the visual acuity dependent on pupil diameter and object distance or state of accommodation.

The present invention is based on analysing the acquired wavefront information of an eye, in particular by analysing the point spread function of the eye. The point spread function is the image that the eye forms of a point source.

The point spread function for a typical eye shows a specific intensity distribution for a corresponding pupil size. When seen in three dimensions, the intensity over the area may be compared to a mountainous area comprising hills and valleys. The peaks of the hills represent the high intensity, whereas the valleys represent areas of lower intensity.

According to the method of the present invention, a point spread function of the eye is analysed by comparing the intensities of the point spread function with a selectable intensity level. The parts of the point spread function having an intensity being larger than the selectable intensity level are determined as relevant part of the PSF. The relevant part represents a cross section through the hills of the point spread function at the selected intensity level. When seen from the top, the cross sections through respective hills in the point spread function form one or more areas. As a further step, an ellipse is drawn which circumscribes the one or more areas formed by the cross sections through the hills. According to the present invention, the result ellipse represents an image quality metric.

According to a preferred embodiment of the present invention, the length of the long axis of the ellipse is taken as an image quality metric. According to a further preferred embodiment of the invention, the relation between the long axis and the short axis of the ellipse is taken as an image quality metric.

Preferably the enclosed area of the ellipse has to be similar to the area of inside the convex hull around the relevant regions.

One way to visualize a convex hull is to put an elastic band around all the points, and let it wrap as tight as it can. The resultant polygon is a convex hull. A more formal mathematical definition is as follows: A convex hull is the smallest convex polygon that contains all points. A polygon is convex if and only if, for any two points inside the polygon, the line segment between these points is inside the polygon.

According to a preferred embodiment of the present invention, the long axis can be substituted by the longest distance in the relevant part of the PSF and the short axis can be substituted by the maximum distance in the perpendicular direction to this axis.

According to a preferred embodiment of the present invention, the enclosed area in between the boundary points of the relevant part of the PSF is taken as an image quality metric.

Best Mode of Fitting the Long Axis and the Short Axis:

A monochromatic PSF for light of the wavelength 550 nm is used. Find the centre of the above described relevant data. The coordinates of the centre are the mean value of the minimum and maximum in each Cartesian direction. As a further step, a circle is drawn around this centre which circumscribes the one or more areas formed by the cross sections through the hills. According to the present invention, the diameter of this circle represents the long axis. As a further step, the area inside the convex hull around the relevant data is determined. The short axis is approximated by following equation:

$$\text{short\_axis} = \text{long\_axis} * (\text{area\_inside\_convex\_hull}/\text{area\_inside\_circle}) \quad (1)$$

According to a preferred embodiment of the present invention, the long and the short axis are transformed into the visual acuity of the eye. Two nearby small objects can be separated by the eye if the centres of their pictures on the retina are separated at least by the length of the long axis of the ellipse. The reciprocal angle between these nearby objects is proportional to the visual acuity. The relation between the long axis and the short axis of the ellipse is taken to derive a correction factor for the visual acuity. The visual acuity is predicted using following equations:

$$\text{VA\_predicted} = d\_\text{VA1}/(\text{long\_axis} * \text{Corr}) \quad (2)$$

$$\text{Corr} = 0.5 * (1 + \text{short\_axis}/\text{long\_axis}) \quad (3)$$

$d\_\text{VA1}$ is the theoretical distance of the centres of retinal pictures of two nearby objects seen under an angle of 1 minute (Definition for a visual acuity of 1 or 20/20). The value of $d\_\text{VA1}$ is approximated with a constant value of 5 µm. VA_predicted is the predicted visual acuity in a decimal scale.

The correction factor is equal to 1 if the long axis is equal to the short axis (circle shape of the relevant area) and it converges to 0.5 for a negligible small short axis. This is in line with observation that an undercorrection in sphere of about −1 dpt causes about twice the decrease in visual acuity compared to an undercorrection in cylinder of −1 dpt.

According to a preferred embodiment of the invention, the method steps are repeated at least one time for the same point spread function using a different selectable intensity level which is preferably smaller or greater than the first selected intensity level. Again, an ellipse is determined which by its form and size represents an image quality metric, wherein preferably the long axis and/or the relation between the long and the short axis of the ellipse is taken as an image quality metric. The selectable intensity level is preferably between 40% to 80% of the maximum of intensity of the point spread function. More preferably, the selectable intensity value is taken from a range of 50% to 70% of the maximum intensity. Most preferably, the selectable intensity value is 60% of the maximum intensity.

According to a further preferred embodiment of the present invention, the method is performed at least one further time for the point spread function of the same eye, but for a different pupil size. Again, the method is preferably performed more than one time by using a selected intensity level.

According to a further preferred embodiment of the present invention, the method is performed for point spread functions of the same eye, but for at least two different states of accommodation the wavefront is modified with different spherical additions. This simulates the cycles of accommodation and relaxation which the eye usually does to find the status for the optimum visual acuity. Also smaller object distances are simulated by modifying the focus. Again, the method is preferably performed more than one time by using a selected intensity level.

For a range of pupil diameters that can be expected under usual daylight conditions and a range of accommodation states of the eye the visual acuity is calculated for the same eye. The highest value of these results is the predicted visual acuity that can be compared with the visual acuity determined using test charts. The pupil size for daylight conditions and the possible accommodation has to be adjusted individually for each eye.

BRIEF DESCRIPTION OF THE DRAWINGS

The invention will be further described by way of examples with reference to the drawings, in which.

DETAILED DESCRIPTION OF THE PREFERRED EMBODIMENTS

Figure 1:
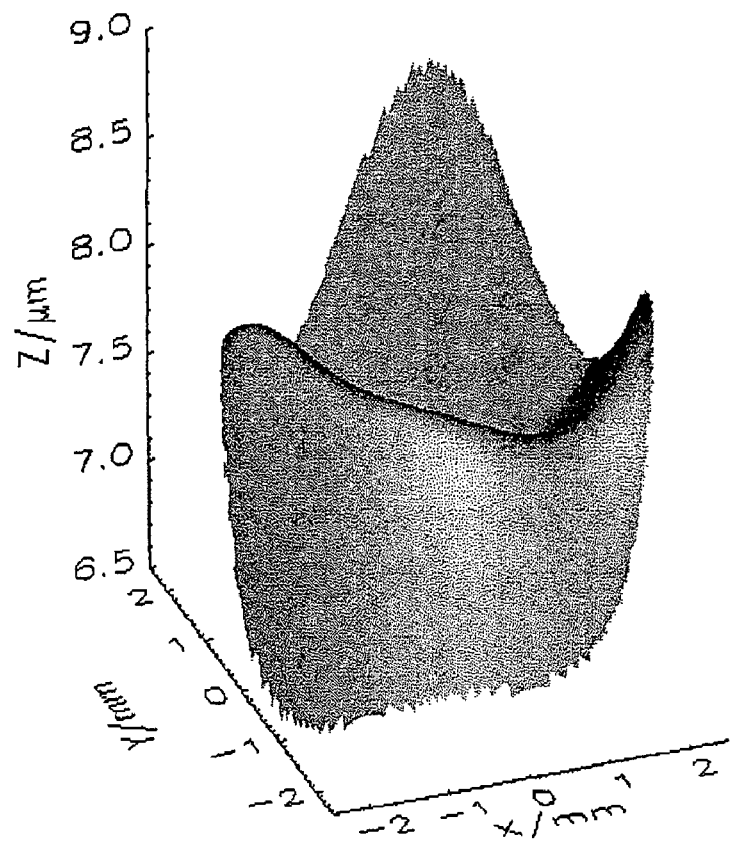
FIG. 1 is a diagram showing a typical wavefront of an eye.

As an example, FIG. 1 depicts a typical wavefront of an eye. This wavefront is shown for the pupil plane of the eye. Such a wavefront may be determined by using any known wavefront sensor as described, e.g., in the documents discussed above. In the present case, the typical wavefront of FIG. 1 is determined based on a best corrected eye, wherein an excimer laser eye surgery system has been used for a non-invasive resculpting of the surface of the eye. Such an excimer laser eye surgery system is described, e.g., in WO 95/27453 A.

More specifically, FIG. 1 shows the wavefront for the pupil plane of the eye with reference to three dimensions of a Cartesian coordinate system. The X-axis and Y-axis are shown here as 1 mm per unit, whereas the Z-axis is shown as 1 μm per unit. The wavefront can be compared to a mountainous area comprising hills and valleys.

Figure 2:
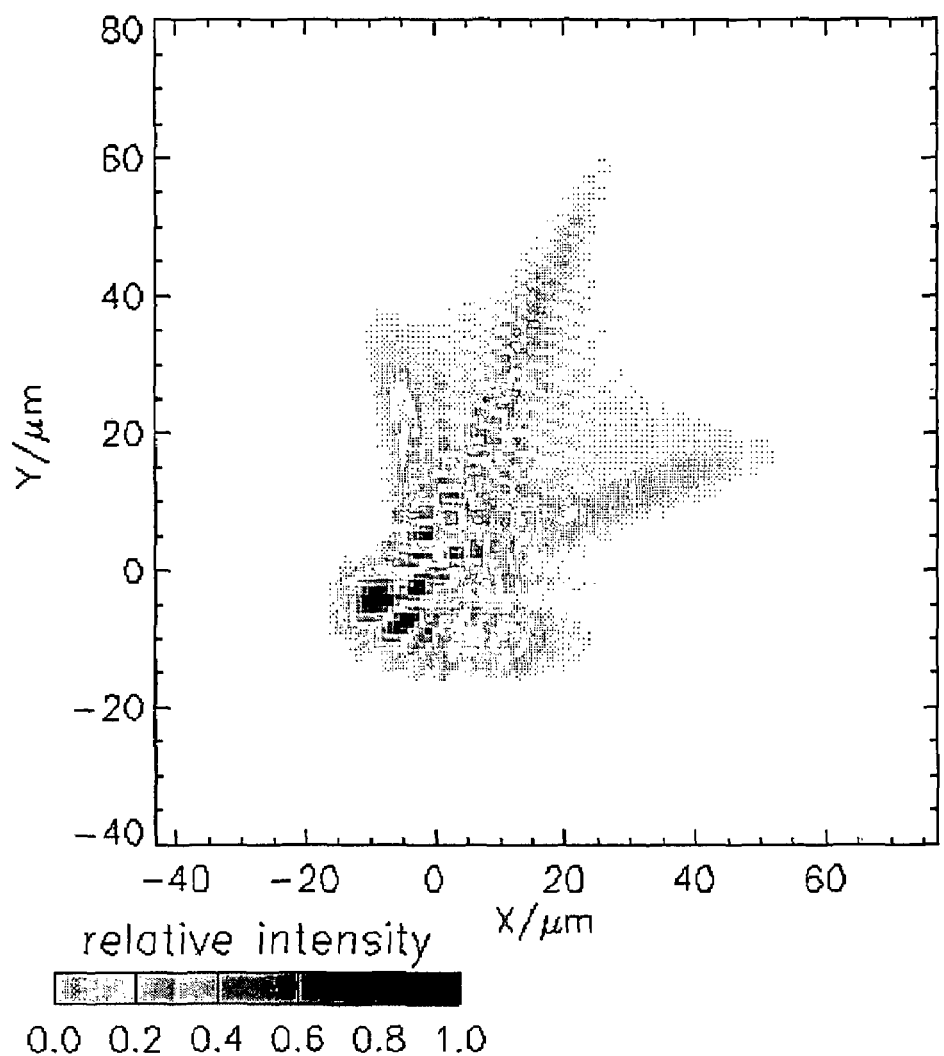
FIG. 2 is the normalised PSF (at the retina of the eye) originating from the wavefront shown in FIG. 1.

FIG. 2 shows a normalised point spread function (PSF) at the retina of the eye originating from the wavefront of FIG. 1 which can be obtained by a known computation as described, e.g., in one of the above discussed documents.

FIG. 2 more specifically shows a two-dimensional diagram, wherein the X-axis and the Y-axis are shown. The units of the X-axis and the Y-axis are given in μm. The legend of FIG. 2 relates to the relative intensity reaching from 0.0 to 1.0 being illustrated as a corresponding grey level from light to dark. The normalised point spread function of FIG. 2 comprises parts with different relative intensities as illustrated by the respective grey level. When seen in three dimensions, the relative intensity over the illustrated area represents a mountainous area comprising hills and valleys of different height. The peaks of the hills shown in FIG. 2 as darker areas represent parts with high relative intensity. Other parts, in particular, the valleys have lower intensity.

According to a preferred embodiment of the present invention, parts of the point spread function having an intensity being larger than the selectable intensity level are determined as relevant part of the PSF. The relevant part can be regarded as a cross-section through the hills of the point spread function at the selected intensity level. This method may also be named a sea-level determination.

Figure 3:
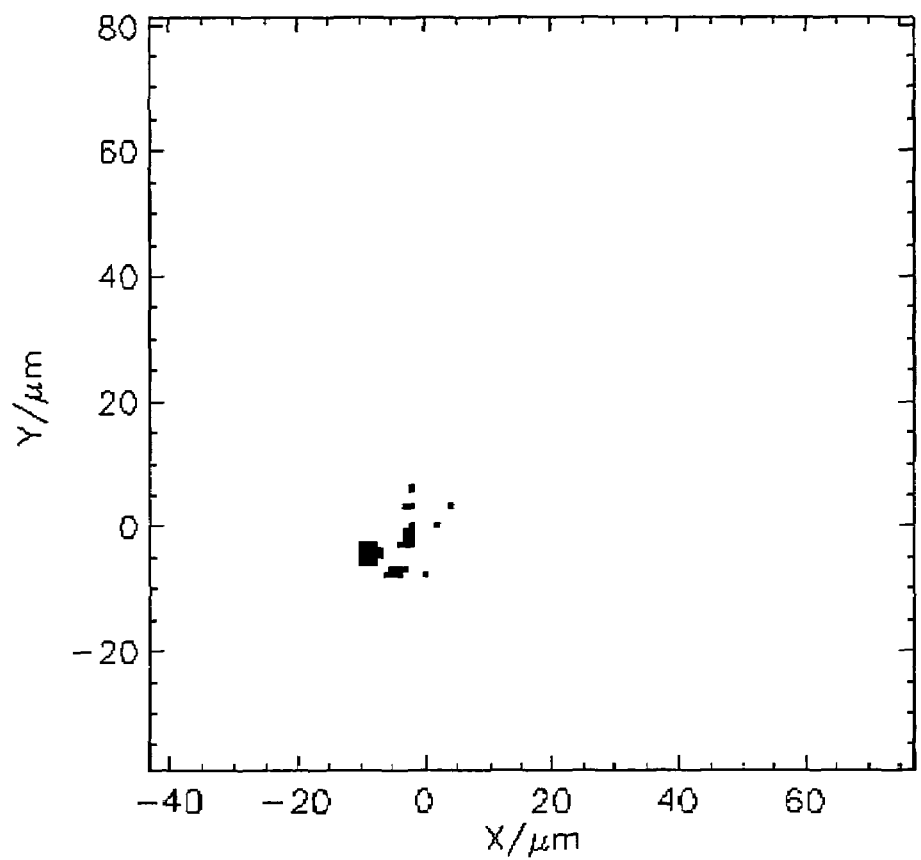
FIG. 3 is a diagram showing parts of the PSF shown in FIG. 2 which are above 50% of the maximum of intensity.

In FIG. 3, the selected intensity level corresponds to 50% of the maximum of intensity. Thus, those parts of the point spread function shown in FIG. 2 having an intensity which is larger than 50% of the maximum of intensity is selected. When seen from the top, the cross-sections through respective hills in the point spread function form several distinct areas. More specifically, there is one distinct larger area at about the coordinate −10 μm, −5 μm, two middle-size areas on the right side from the larger area and five small areas at the right side from the middle-size areas and above the middle-size areas. All areas represent the relevant part of the point spread function, which is used for determining an image quality metric, as will be discussed hereunder.

Figure 4:
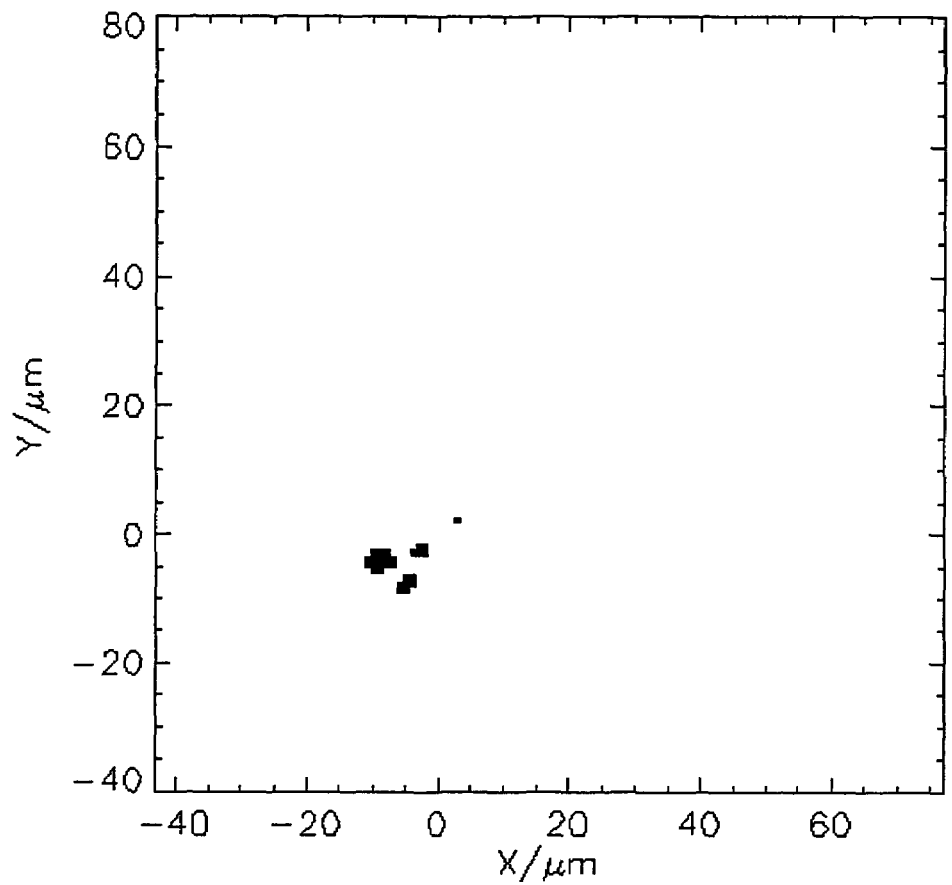
FIG. 4 is a diagram showing parts of the PSF shown in FIG. 2 which are above 60% of the maximum of intensity.

FIG. 4 shows the relevant parts representing a cross-section through the hills of the point spread function of FIG. 2 and the selected intensity level corresponds to 60% of the maximum of intensity. Here one larger area, two middle-size areas, and one small area are shown.

Figure 5:
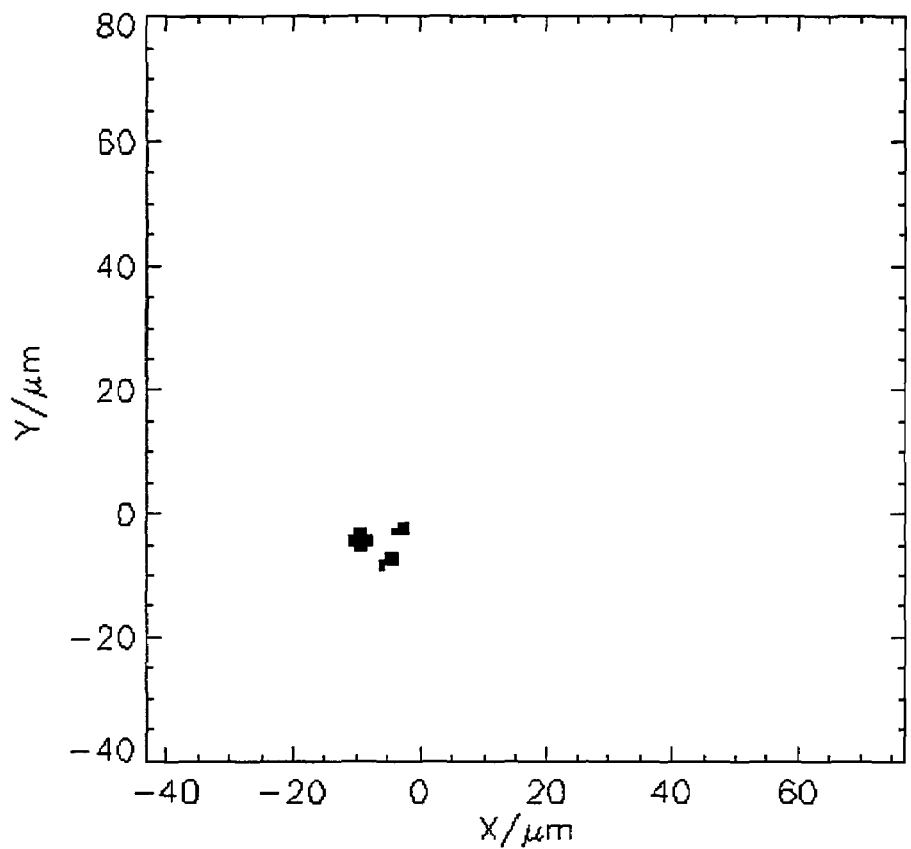
FIG. 5 is a diagram showing parts of the PSF shown in FIG. 2 which are above 65% of the maximum of intensity.

FIG. 5 shows the relevant part representing a cross-section through the hills of the point spread function shown in FIG. 2 above the selected intensity level of 65% of the maximum of intensity. Here one larger and two middle-size parts remain.

Figure 6:
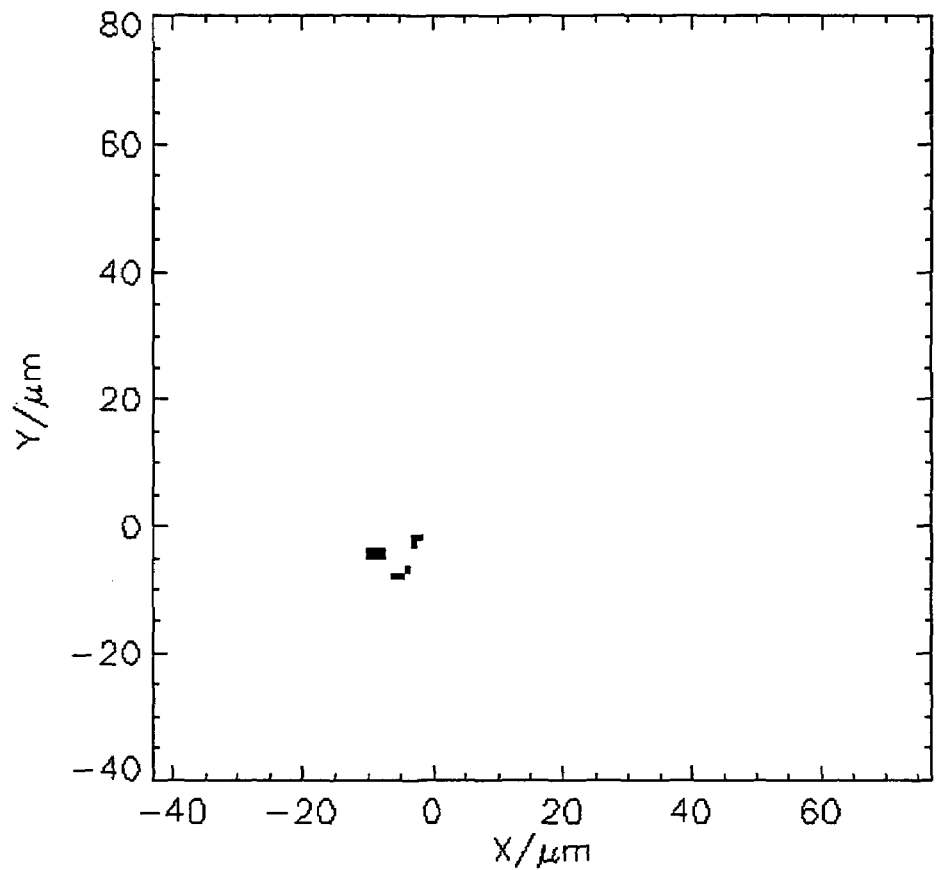
FIG. 6 is a diagram showing parts of the PSF shown in FIG. 2 which are above 75% of the maximum of intensity.

FIG. 6 shows the relevant part representing a cross-section through the hills of the point spread function as shown in FIG. 2 above the selected intensity level of 75% of the maximum of intensity. Here one middle-size area and two smaller areas remain.

When comparing the parts of the point spread function shown in FIGS. 3, 4, 5 and 6, it is apparent that a smaller number of areas remain and/or that the corresponding areas are getting smaller when increasing the value of the selected intensity level. Each of the relevant parts shown in one of FIGS. 3-6 can be used for determining an image quality metric as discussed in the following.

Figure 7:
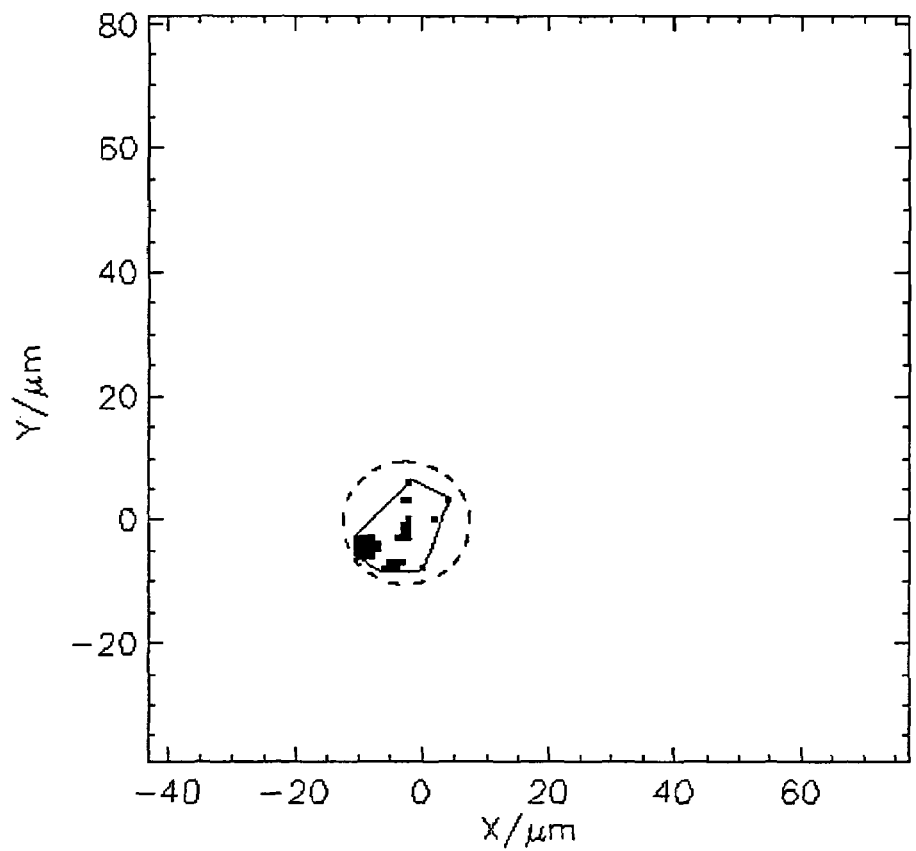
FIG. 7 is a diagram showing parts of the PSF shown in FIG. 2 which are above 50% of the maximum of intensity, wherein the convex hull is shown by a solid line and the circle circumscribing the parts of the PSF is shown by a dashed line.

FIG. 7 shows the parts of the point spread function of FIG. 2, which are above 50% of the maximum of intensity similar to FIG. 3. It further shows a circle drawn as a dashed line which circumscribes all areas representing the relevant parts of the point spread function. According to this preferred embodiment, at first the centre of the circle is determined as follows. The minimum value and the maximum value in each Cartesian direction, i.e., along the X-axis and along the Y-axis is determined. Then the mean value with the minimum and the maximum value along the X-axis and the mean value of the minimum and the maximum value along the Y-axis is determined. Both mean values represent the coordinates of the centre of the circle. At a further step, a circle is drawn around this centre such that all areas of the relevant part of the point spread function are circumscribed as shown. In the example of FIG. 7, the centre is at about the coordinates 0, 0. The radius is determined by the lowermost left corner of the larger area shown herein.

According to a further preferred embodiment of the present invention, a convex hull is shown by a solid line. The solid line connects all areas of the relevant parts by straight lines such that all areas are within the area circumscribed by the solid line as shown in FIG. 7. At a further step, the area inside the hull is determined.

Figure 8:
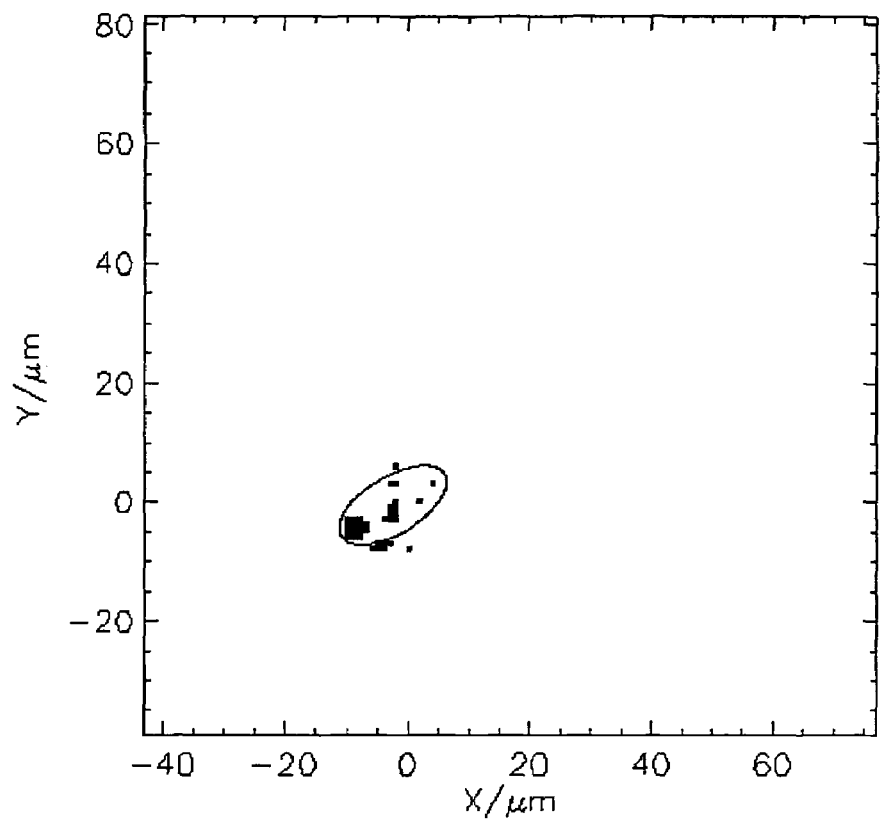
FIG. 8 is a diagram showing parts of the PSF shown in FIG. 2 which are above 50% of the maximum of intensity, wherein an ellipse is shown by a solid line which is fitted to the parts of the PSF.

FIG. 8 shows parts of the point spread function shown in FIG. 2 which are above 50% of the maximum intensity similar to FIG. 3 and FIG. 7. Herein an ellipse is fitted by using the area inside of the hull and the circle shown in FIG. 7. More specifically, according to this preferred embodiment of the present invention, the diameter of the circle shown in FIG. 7 represents the long axis of the ellipse. The direction of the long axis is determined based on the longest distance between distinct areas of the relevant parts. This short axis is approximated by the above-mentioned equation (1). Thus, the length of the long axis corresponding to the diameter of the circle is taken as one factor. The other factor is obtained by dividing the area inside the hull by the area inside the circle. Thus, the short axis corresponds to a predetermined proportion of the long axis. The long axis and the short axis (not shown in FIG. 8) are used for drawing the ellipse in FIG. 8.

The ellipse as shown in FIG. 8 represents a visual acuity metric. More specifically, a patient having an eye with a wavefront as shown in FIG. 1 and a PSF as shown in FIG. 8 has a specific visual acuity which is better in the direction of the short axis of the ellipse and which is worse in the direction of the long axis of the ellipse.

As discussed before, the visual acuity is predicted using the above equation (2). This equation (2) takes into account the theoretical distance of the centres of retinal pictures of two nearby objects seen under an angle of 1 minute. This is the known definition for a visual acuity of 1.0 or 20/20. For an average eye, the value of d_VA1 is approximated with a constant value of 5 μm. The predicted visual acuity VA_predicted is given as a decimal scale. It corresponds to the product, wherein the first factor is the division of d_VA1 by the length of the long axis and the other factor is a correction factor Corr. The correction factor is calculated using equation (3) from the relationship between the length of the short axis and the length of the long axis. This value is added to one. The resulting sum divided by two corresponds to the correction factor.

The present invention is particularly suitable for determining the visual acuity objectively. This objective visual acuity metric can be used, e.g., for determining the visual acuity of a patient's eye before a treatment and after a treatment, e.g., a treatment for visual correction by using an excimer laser system.

The example of a typical wavefront as described with reference to FIG. 1 and the corresponding point spread function as shown in FIG. 2 is exemplary for a particular pupil size and a particular state of accommodation of the eye. The determination of the visual acuity can be repeated at least once for the point spread function of the same eye, but at least for one other pupil size and/or for at least one other state of accommodation of the eye.

Figure 9:
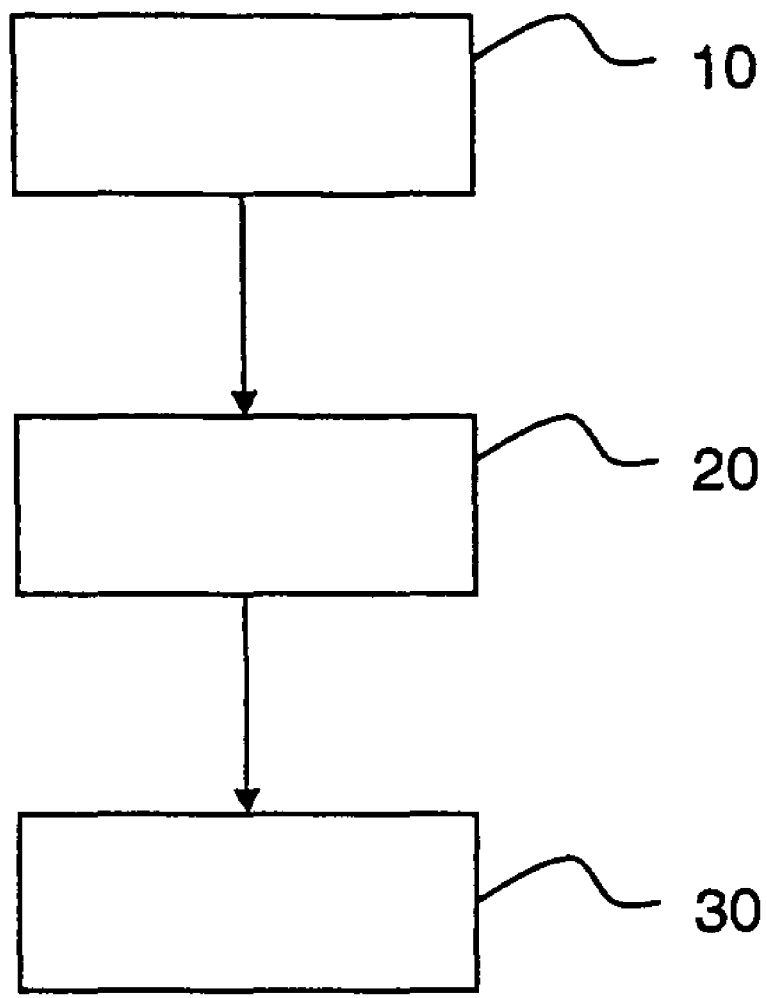
FIG. 9 is a block diagram of a preferred embodiment of the invention.

FIG. 9 shows a block diagram of a preferred embodiment of an apparatus according to the present invention. It comprises a device 10 for measurement of an eye which provides wavefront data. The wavefront data are transferred to a calculation device 20, such as a personal computer. The calculation device 20 performs the calculation based on the wavefront data and provides its results to an output device 30 such as a monitor.

Figure 10:
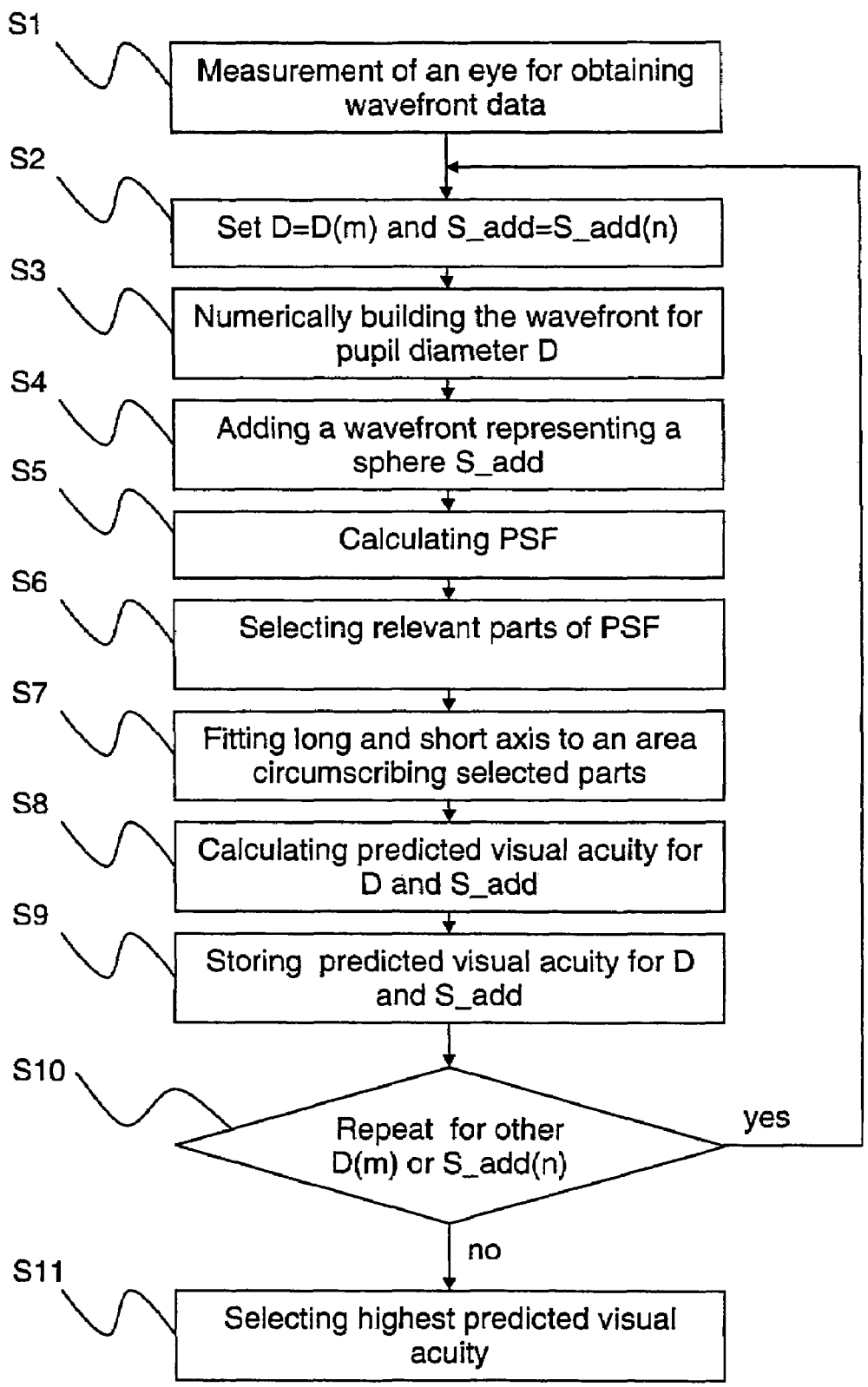
FIG. 10 is a flow diagram for performing a preferred embodiment of the present invention.

FIG. 10 shows a flow chart for performing a preferred embodiment of a method according to the present invention. In a first step S1, wavefront data of an eye are obtained by performing a measurement using, e.g., the measurement device 10 of FIG. 9. In step S2, a specific pupil diameter D is set. This pupil diameter can be set automatically or can be input manually by a user. Furthermore, the value S_add is set. This wavefront is added to simulate different accommodation of the eye and different distances of the target.

In a further step S3, the wavefront is built numerically based on the wavefront data obtained in step S1 for the specific pupil diameter D being set in step S2. In step S4, the sum of the numerically built wavefront and the wavefront representing the sphere S_add is determined. Based on this sum, a point spread function PSF is calculated therefrom in step S5. Relevant parts of the point spread function are selected in step S6 by, e.g., comparing the intensities of the point spread function with a selectable intensity level of intensity and selecting only those parts of the point spread function having an intensity being larger than the selectable intensity level. In step S7, a long and a short axis are fitted to an area circumscribing said selected parts of the point spread function. Thereafter, in step S8, the predicted visual acuity is calculated based on information with respect to the long and short axis determined in step S7. This calculated visual acuity relates to the specific pupil diameter D and specific wavefront corresponding to the sum calculated in step S4. In step S10, a decision is made whether steps S2 to S9 are repeated for another pupil diameter D(m) and another spherical addition S_add(n). Thus, steps S2 to S9 will be repeated automatically for specific values D(1), D(2), D(3), . . . D(m) and/or S_add (1), S_add(2), S_add(3), . . . S_add(n) in a given range of pupil diameters and spherical additions, wherein said given range can be set automatically or inputted manually by a user. If steps S2 to S9 should not be repeated anymore, the highest predicted visual acuity can be selected in step S11. It is also possible to select not only one but several predicted visual acuities and to transfer these results to an output device like a monitor 30.

The foregoing disclosure and description of the invention are illustrative and explanatory thereof and various changes, in particular, of the method of operation may be made without departing from the scope of the invention.

The invention claimed is:

1. Method for determining the visual acuity of an eye comprising the steps of:
   providing the wavefront information of the eye,
   generating a point spread function based on the wavefront information of the eye, said point spread function representing a specific intensity distribution for a corresponding pupil size,
   comparing the intensities of the point spread function with a selectable intensity level of intensity,
   determining those parts of the point spread function having an intensity being larger than the selectable intensity level as a relevant part of the point spread function.

2. Method according to claim 1, further comprising the step of drawing an ellipse which circumscribes the relevant part of the point spread function.

3. Method according to claim 2, further comprising the step of determining the length of the long axis of the ellipse.

4. Method according to claim 3, further comprising the step of determining the length of the short axis of the ellipse and determining the relation between the long axis and the short axis of the ellipse.

5. Method according to claim 1, further comprising the step of determining the longest distance along a first axis in the relevant part of the point spread function.

6. Method according to claim 5, further comprising the step of determining the maximum distance along a second axis in the relevant part of the point spread function in a direction perpendicular to the first axis.

7. Method according to claim 1, further comprising the step of determining the enclosed area in between boundary points of the relevant part of the point spread function.

8. Method according to claim 1, wherein a long and/or a short axis perpendicular to each other are determined based on the relevant part of the point spread function and further comprising the step of transforming said long and said short axis into a value representing the visual acuity of the eye.

9. Method according to claim 8, further comprising the step of determining the relation between the long axis and the short axis and deriving a correction factor for the visual acuity.

10. Method according to claim 1, wherein a circle is determined which circumscribes the relevant part of the point spread function, wherein the centre of the circle is determined as the mean value of the minimum value and maximum value of any relevant part along the X-axis and the mean value of the minimum value and the maximum value of any relevant part along the Y-axis.

11. Method according to claim 10, further comprising the step of determining the area of the circle, wherein the diameter of the circle is taken as the length of the long axis and wherein the short axis is determined based on the relationship between the area of the surface and the enclosed area in between boundary points of the relevant part of the point spread function.

12. Method according to claim 1, wherein said selectable intensity level is between 40% to 80% of the maximum of intensity of the point spread function.

13. Method according to claim 1, wherein the selectable intensity level is between a range of 50% to 70% of the maximum intensity of the point spread function.

14. Method according to claim 1, comprising generating the point spread function of the same eye, but at least for one other pupil size.

15. Method according to claim 1, comprising repeating the method by using at least one other selectable intensity level.

16. Method according to claim 1, comprising repeating the method for a point spread function of the same eye, but for at least two different states of accommodation of the eye wherein the wavefront is modified with different spherical additions.

17. Method according to claim 16, comprising repeating the method at least two times using different selectable intensity levels.

18. Method according to claim 16, wherein the predicted best visual acuity for any of the at least two different states of accommodation of the eye is selected as the nominal visual acuity.

19. Apparatus for determining the visual acuity of an eye comprising:

means for providing the wavefront information of the eye, means for generating a point spread function based on the wavefront information of the eye, said point spread function representing a specific intensity distribution for a corresponding pupil size, comparator for comparing the intensities of the point spread function with a selectable intensity level, means for determining those parts of the point spread function having an intensity being larger than the selectable intensity level as a relevant part of the point spread function.

20. Apparatus according to claim 19, further comprising calculating means for determining an ellipse which circumscribes the relevant part of the point spread function.

21. Apparatus according to claim 20, wherein said calculating means determine the length of the long axis of the ellipse.

22. Apparatus according to claim 21, wherein said calculating means determine the length of the short axis of the ellipse and determine the relation between the long axis and the short axis of the ellipse.

23. Apparatus according to claim 19, further comprising calculating means for determining the longest distance along a first axis in the relevant part of the point spread function.

24. Apparatus according to claim 23, wherein said calculating means determine the maximum distance along a second axis in the relevant part of the point spread function in a direction perpendicular to the first axis.

25. Apparatus according to claim 19, further comprising calculating means for determining the enclosed area in between boundary points of the relevant part of the point spread function.

26. Apparatus according to claim 19, wherein a long and/or a short axis perpendicular to each other are determined based on the relevant part of the point spread function and further comprising means for transforming said long and said short axis into a value representing the visual acuity of the eye.

27. Apparatus according to claim 26, further comprising means for determining the relation between the long axis and the short axis and deriving a correction factor for the visual acuity.

28. Apparatus according to claim 27, wherein at least two different selectable intensity levels are used.

29. Apparatus according to claim 19, comprising means for determining a circle which circumscribes the relevant part of the point spread function, wherein the centre of the circle is determined as the mean value of the minimum value and maximum value of any relevant part along the X-axis and the mean value of the minimum value and the maximum value of any relevant part along the Y-axis.

30. Apparatus according to claim 29, further comprising means for determining the area of the circle, wherein the diameter of the circle is taken as the length of the long axis and wherein the short axis is determined based on the relationship between the area of the surface and the enclosed area in between boundary points of the relevant part of the point spread function.

31. Apparatus according to claim 19, wherein said selectable intensity level is between 40% to 80% of the maximum of intensity of the point spread function.

32. Apparatus according to claim 19, wherein the selectable intensity level is between a range of 50% to 70% of the maximum intensity of the point spread function.

33. Apparatus according to claim 19, wherein the point spread function of the same eye, but at least for one other pupil size is generated.

34. Apparatus according to claim 19, wherein at least one other selectable intensity level is used.

35. Apparatus according to claim 34, wherein the predicted best visual acuity for any of the at least two different states of accommodation of the eye is selected as the nominal visual acuity.

36. Apparatus according to claim 19, wherein a point spread function of the same eye, but for at least two different states of accommodation of the eye is used wherein the wavefront is modified with different spherical additions.

* * * * *